(12) United States Patent
Ross

(10) Patent No.: US 8,593,154 B2
(45) Date of Patent: Nov. 26, 2013

(54) SYSTEM AND METHOD FOR ARTIFACT SUPPRESSION IN SOFT-FIELD TOMOGRAPHY

(75) Inventor: Alexander Seth Ross, Albany, NY (US)

(73) Assignee: General Electric Company, Niskayuna, NY (US)

( * ) Notice: Subject to any disclaimer, the term of this patent is extended or adjusted under 35 U.S.C. 154(b) by 390 days.

(21) Appl. No.: 12/978,466

(22) Filed: Dec. 24, 2010

(65) Prior Publication Data

US 2012/0161782 A1 Jun. 28, 2012

(51) Int. Cl.
*G01R 27/00* (2006.01)
(52) U.S. Cl.
USPC .......................... 324/600; 324/76.11
(58) Field of Classification Search
USPC .................. 324/600, 71.1, 307–310
See application file for complete search history.

(56) References Cited

U.S. PATENT DOCUMENTS

| | | | |
|---|---|---|---|
| 5,919,142 A | 7/1999 | Boone et al. | |
| 6,236,886 B1 | 5/2001 | Cherepenin et al. | |
| 6,397,095 B1 | 5/2002 | Eyuboglu et al. | |
| 6,577,700 B1 * | 6/2003 | Fan et al. | 378/4 |
| 6,882,879 B2 | 4/2005 | Rock | |
| 7,169,107 B2 | 1/2007 | Jersey-Willuhn et al. | |
| 7,435,226 B2 | 10/2008 | Suarez | |
| 7,660,617 B2 | 2/2010 | Davis | |
| 2002/0101237 A1 * | 8/2002 | Miyosi et al. | 324/307 |
| 2010/0127705 A1 | 5/2010 | Scharfetter | |

FOREIGN PATENT DOCUMENTS

WO 2007128952 A1 11/2007

OTHER PUBLICATIONS

Hamid Dehghani et, al., Numerical Modelling Errors in Electrical Impedance Tomography, Physiological Measurement, vol. 28, No. 7.
Search Report and Written Opinion from corresponding EP Application No. 11193925.2-1526 dated Apr. 19, 2012.
Casanas R. et al., "Biological tissue characterization by magnetic induction spectroscopy (MIS): requirements and limitations", vol. 50, No. 7, pp. 870-880, Jul. 1, 2003.
Manuchehr Soleimani, "Computational Aspects of Low Frequency Electrical and Electromagnetic Tomography: A Review Study", International Journal of Numerical Analysis and Modeling, vol. 5, No. 3, pp. 407-440, Jan. 1, 2008.
Jin Keun Seo et al., "Frequency-difference electrical impedance tomography (fdEIT): algorithm development and feasibility study; Feasibility of frequency-difference EIT", Physiological Measurement, vol. 29, No. 8, pp. 929-944, Aug. 1, 2008.
System and Method for Soft-Field Tomography Data Acquisition, U.S. Appl. No. 13/070,294, filed Mar. 23, 2011.
System and Method for Correcting Fault Conditions in Soft Field Tomography, U.S. Appl. No. 12/976,656, filed Dec. 22, 2010.
System and Method for Soft Field Reconstruction, U.S. Appl. No. 12/973,734, filed Dec. 20, 2010.
System and Method for Transducer Placement in Soft Field Tomography, U.S. Appl. No. 13/406,236, filed Feb. 27, 2012.
System and Method for Determining Physiological Parameters Based on Electrical Impedance Measurements, U.S. Appl. No. 12/973,718, filed Dec. 20, 2010.
System and Method for Excitation Generation in Soft Field Tomography, U.S. Appl. No. 13/179,179, filed Jul. 8, 2011.

* cited by examiner

*Primary Examiner* — Vincent Q Nguyen
(74) *Attorney, Agent, or Firm* — Jenifer Haeckl

(57) ABSTRACT

A system and method for artifact suppression in soft-field tomography are provided. One method includes obtaining an excitation pattern and applying the excitation pattern to an object, wherein the excitation pattern includes a plurality of frequency components. The method also includes measuring a response at one or more of a plurality of transducers coupled to the object and separating the responses among the plurality of frequency components to suppress one or more artifacts.

21 Claims, 5 Drawing Sheets

SYSTEM AND METHOD FOR ARTIFACT SUPPRESSION IN SOFT-FIELD TOMOGRAPHY

BACKGROUND

This subject matter disclosed herein relates generally to data reconstruction systems and methods, and more particularly to systems and methods to identify and suppress artifacts in soft-field tomography.

Soft-field tomography, such as Electrical Impedance Spectroscopy (EIS) (also referred to as Electrical Impedance Tomography (EIT)), diffuse optical tomography, elastography, and related modalities may be used to measure the internal properties of an object, such as the electrical properties of materials comprising internal structures of an object (e.g., a region of a human body). For example, in EIS systems, an estimate is made of the distribution of electrical conductivities of the internal structures. Such EIS systems reconstruct the conductivity and/or permittivity of the materials within the area or volume based on an applied excitation (e.g., current) and a measured response (e.g., voltage) acquired at a surface of the area or volume. Visual distributions of the estimates can then be formed.

In EIS, the complex conductivity distributions within a volume are determined using assumed known applied electrical excitations, apriori geometry and surface electrode data, and signal measurement data from transducers coupled to the volume under test. An electromagnetic model with assumptions about the volume and electrode geometry, boundary conditions, the applied excitation, and the interior conductivity distribution are then used to determine a predicted response to a given excitation. The inverse problem in EIS is to determine the spatial distribution of complex conductivities that give rise to the difference between measured data and the predicted model data.

The EIS inverse problem is highly ill-posed in that large perturbations in the conductivity distribution may result in small changes in the measurement data. Similarly, small changes or errors in the applied excitation may result in large changes in the measured data. The solution to the inverse problem is the complex conductivity distribution, within the assumed volume and electrode geometry, which accounts for differences in the measured data from the data predicted by a forward model. In addition to conductivity distribution differences, differences between modeled and experimental excitation, differences between modeled and experimental surface geometry, and differences between electrode size, position, arrangement, among others can also account for the differences between prediction data and measured data.

Thus, EIS reconstructions of conductivity distributions may inherently suffer from artifacts due to experimental geometry and electrode mismatch to the forward prediction model.

BRIEF DESCRIPTION

In accordance with an embodiment, a method for acquiring soft-field tomography data is provided. The method includes obtaining an excitation pattern and applying the excitation pattern to an object, wherein the excitation pattern includes a plurality of frequency components. The method also includes measuring a response at one or more of a plurality of transducers coupled to the object and separating the responses among the plurality of frequency components to suppress one or more artifacts.

In accordance with another embodiment, a soft-field tomography system is provided that includes a plurality of transducers configured for positioning proximate a surface of an object. The soft-field tomography system also includes one or more excitation drivers coupled to the plurality of transducers and configured to generate excitation signals for the plurality of transducers, wherein the excitation signals include a plurality of frequency components. The soft-field tomography system also includes one or more response detectors coupled to the plurality of transducers and configured to measure a response of the object at the plurality of transducers to the excitation applied by the plurality of transducers based on the excitation signals. The soft-field tomography system further includes a soft-field reconstruction module configured to reconstruct a property distribution based on the excitation signals and the measured response based in part on a difference between the responses among the plurality of frequency components.

In accordance with yet another embodiment, a computer readable storage medium for acquiring soft-field tomography data and reconstructing a property distribution of an object using a processor is provided. The computer readable storage medium including instructions to command the processor to obtain an excitation pattern, apply the excitation pattern to an object, wherein the excitation pattern includes a plurality of frequency components, and measure a response at one or more of a plurality of transducers coupled to the object. The instructions also command the processor to determine a difference between the responses for each of the plurality of frequency components and use the measured response and the difference to reconstruct a property distribution of the object.

BRIEF DESCRIPTION OF THE DRAWINGS

The presently disclosed subject matter will be better understood from reading the following description of non-limiting embodiments, with reference to the attached drawings, wherein below.

DETAILED DESCRIPTION

Figure 1:
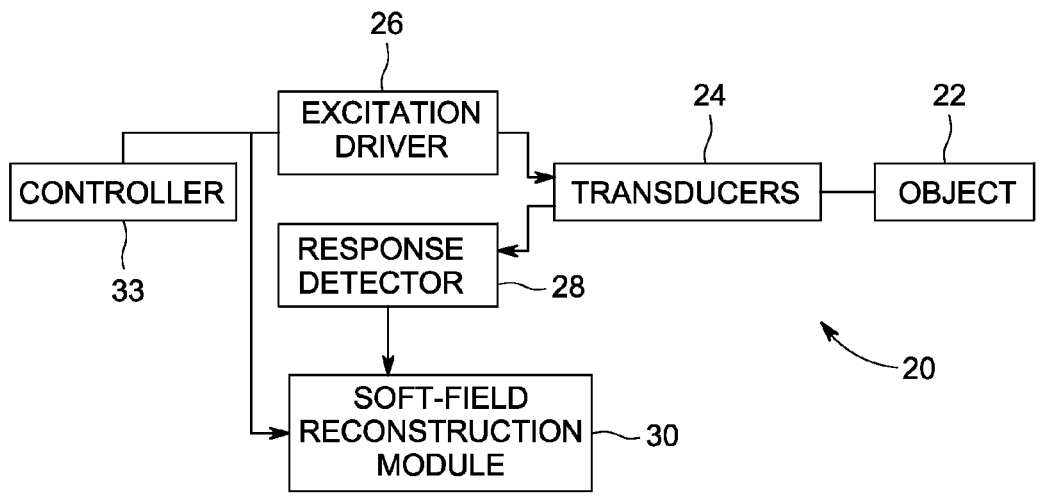
FIG. 1 is a simplified block diagram illustrating a soft-field tomography system formed in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, circuits or memories) may be implemented in a single piece of hardware or multiple pieces of hardware. It should be understood that the various embodiments are not limited to the arrangements, component/element interconnections and instrumentality shown in the drawings.

As used herein, a module or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" a module or a plurality of modules having a particular property may include additional such modules not having that property.

Various embodiments provide a system and method for suppressing artifacts related to the differences between the modeled and actual geometry of at least one of the transducer arrangement, boundary, surface and/or object in soft-field tomography systems, such as Electrical Impedance Spectroscopy (EIS) or Electrical Impedance Tomography (EIT) systems. However, the various embodiments may apply to other soft-field tomography systems, such as Diffuse Optical Tomography (DOT), Near InfraRed Spectroscopy (NIRS), thermography, elastography or microwave tomography, and related modalities.

In various embodiments, geometric and transducer placement artifacts are identified and suppressed. In particular, one or more embodiments perform the suppression based on the knowledge that many materials, including biological and biomedical materials exhibit a strong frequency dependence in the complex conductivity for these materials, while geometric effects do not have this frequency dependence in measured data. A technical effect of at least one embodiment is discriminating and suppressing geometric and transducer placement artifacts. Another technical effect of at least one embodiment is relaxing the requirement for accurate geometric modeling in soft-field tomography reconstructions.

It should be noted that suppressing artifacts as used herein means that the effects caused by artifacts are reduced, which may reduced be in part or entirely, and which may relate to artifacts from different sources. It also should be noted that as used herein, "soft-field tomography" refers generally to any tomographic or multidimensional extension of a tomographic method that is not "hard-field tomography".

Figure 2:
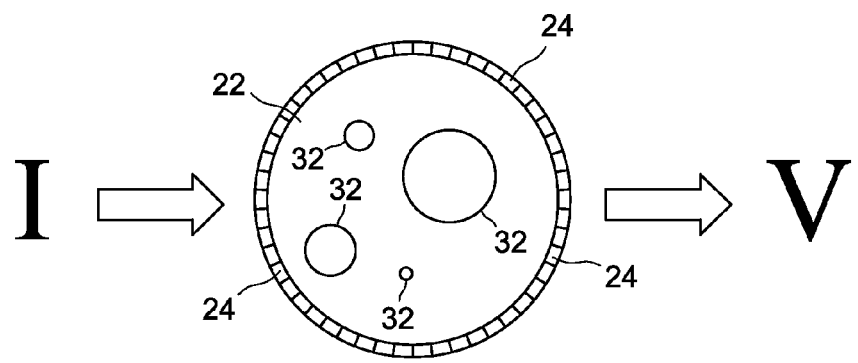
FIG. 2 is a simplified diagram illustrating reconstruction of a property distribution.

One embodiment of a soft-field tomography system 20 is illustrated in FIG. 1. For example, the soft-field tomography system 20 may be an Electrical Impedance Spectroscopy (EIS) system, also referred to as Electrical Impedance Tomography (EIT) system used to determine the electrical properties of materials within an object 22 as illustrated in FIG. 2. For example, the spatial distribution of electrical conductivity ($\sigma$) and/or permittivity ($\epsilon$) may be determined inside the object 22 or other area or volume. Thus, internal properties of the object 22 (e.g., a patient) may be determined. In the illustrated embodiment, the system 20 includes a plurality of transducers 24 (e.g., electrodes) that are positioned at or proximate a surface of the object 22, which in a healthcare application (e.g., patient monitoring or tissue characterization) may include attaching the plurality of the transducers 24 to the skin of a patient or subject. For example, the transducers 24 may be positioned on the surface of the object 24 (e.g. electrodes, thermal sources, ultrasound transducers), near the surface of the object 24 (e.g., radiofrequency antenna), or penetrating the surface of the object 24 (e.g., needle electrodes). Thus, the transducers 24 may take different forms, such as surface-contacting electrodes, standoff electrodes, capacitively coupled electrodes, conducting coils, and antennas, among others.

An excitation driver 26 and a response detector 28 are coupled to the transducers 24, which are each connected to a soft-field reconstruction module 30. The soft-field reconstruction module 30 may be any type of processor or computing device that performs soft-field reconstruction based at least in part on received responses from the transducers 24 and that suppresses geometry and object property differences from baseline assumptions as described in more detail herein. For example, the soft-field reconstruction module 30 may be hardware, software or a combination thereof. In one embodiment, the excitation driver 26 and the response detector 28 are physically separate devices. In other embodiments, the excitation driver 26 and the response detector 28 are physically integrated as one element. A controller 33 is also provided and sends instructions to the excitation driver 26 that drives the transducers 24 based on the instructions. It should be noted that an excitation driver 26 may be provided in connection with all of the transducers 24 or a subset of the transducers 24.

It also should be noted that different types of excitations may be used to obtain property distribution data for use in the reconstruction process. For example, electrical, magnetic, optical, thermal or ultrasound excitations, among others, may be used in combination with the various embodiments. In these different embodiments, the transducers 24 may be coupled to the object 22 in different ways and not necessarily in direct contact or only at a surface of the object 22 (e.g., coupled electrically, capacitively, galvanically, etc.).

In one embodiment, the object 22 is a human body region, such as a head, a chest, or a leg, wherein air, blood, muscle, fat, and other tissues have different electrical conductivities. The soft-field tomography system 20 estimates or determines conditions of the internal properties (e.g., material properties) of the human body region, and thus can assist in the diagnoses of diseases, for example, associated with hemorrhage, tumor, and lung function, among others. The object is not limited to humans and animals are also subject to the techniques detailed herein. In other embodiments, the soft-field tomography system 20 can be used for generating a visual representation of the electrical impedance distribution in a variety of other applications, such as for determining the material properties in a mixed flow including oil and water, or for an underground earth area for soil analysis and roadbed inspection, among others.

In various embodiments, the transducers 24 are formed from any suitable material. For example, the types of transducer 24 used may be based on the particular application, such that a corresponding transducer type (e.g., electrode, coil, etc.) is used to generate the soft-field excitations (e.g., electromagnetic field) and receive responses of the object to the excitations for the particular application. In some embodiments, a conductive material may be used to establish electrical current. For example, the transducers 24 may be formed from one or more metals such as copper, gold, platinum, steel, silver, and alloys thereof. Other exemplary materials for forming the transducers 24 include non-metals that are electrically conductive, such as a silicon based materials used in combination with micro-circuits. In one embodiment, where the object 22 is a human body region, the transducers 24 are formed from silver-silver chloride. Additionally, the transducers 24 may be formed in different shapes and/or sizes, for example, as rod-shaped, flat plate-shaped, or needle-shaped structures. It should be noted that in some embodiments, the transducers 24 are insulated from one another. In other embodiments, the transducers 24 can be positioned in direct ohmic contact with the object 22 or be capacitively coupled to the object 22.

In operation, the transducers 24 or a subset of the transducers 24 may be used to transmit signals (e.g., deliver or modulate signals), for example, deliver electrical current continuously or to deliver a time-varying signal such that excitations may be applied across a temporal or varying frequency range (e.g., 1 kHz to 1 MHz) to the object 22 to generate an electromagnetic (EM) field within the object 22. In an EIS or EIT application, the resulting surface potentials, namely the voltages on the transducers 24 are measured to determine an electrical conductivity or permittivity distribution using one or more suitable reconstruction method, which may suppress artifacts using frequency difference information or frequency difference and time difference information as described herein. For example, a visual distribution may be reconstructed based on the geometry of the transducers 24, the applied currents and the measured voltages.

Thus, in various embodiments, the excitation driver 26 applies an excitation to each of the transducers 24 and the response detector 28 measures a response of the object 22 at each of the transducers 24 (which may be multiplexed by a multiplexer) in response to the excitation applied on the transducers 24. It should be noted that any type of excitation may be provided, for example, electrical current, electrical voltage, a magnetic field, a radio-frequency wave, a thermal field, an optical signal, a mechanical deformation and an ultrasound signal, among others.

For example, in an EIS or EIT application, and as illustrated in FIG. 2, a soft-field reconstruction is performed to identify regions of interest 32 within the object 22. As shown, the response detector 28 (shown in FIG. 1) measures a response voltage (or a response current) on the transducers 24 in response to the current (or voltage) applied by the excitation driver 26 (shown in FIG. 1) to the transducers 24.

It should be noted that the response detector 28 also may include one or more analog-signal-conditioning elements (not shown) that amplifies and/or filters the measured response voltage or current. In other embodiments, a processor of the soft-field tomography system 20 includes a signal conditioning element for amplifying and/or filtering the response voltage or response current received from the response detector 28.

Figure 3:
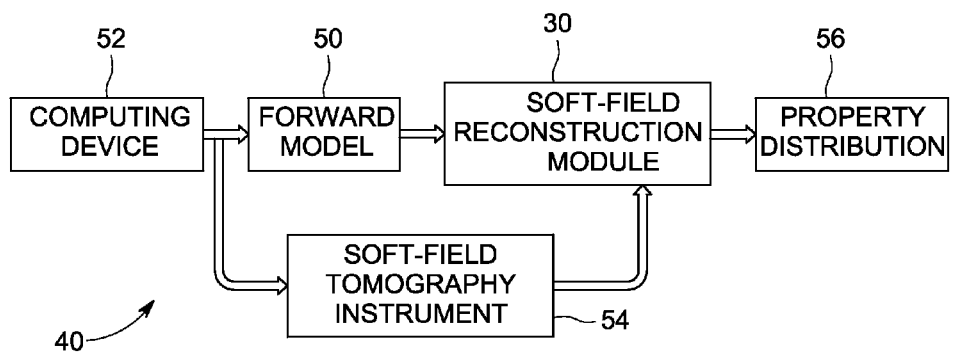
FIG. 3 is a block diagram illustrating soft-field tomography information flow in accordance with various embodiments.

The soft-field reconstruction module 30, thus, computes a response of the object 22 to the applied excitation. For example, an EIS information flow 40 is illustrated in FIG. 3. In particular, a forward model 50 is used based on excitations from a computing device 52, to predict voltages (predicted data), which are provided to the soft-field reconstruction module 30. In one embodiment, an inverse problem relating the measured responses (e.g., measured signals), and the applied excitations, and the electrical conductivity distribution inside of the object 22 being tested or interrogated by the soft-field tomography system 20 is solved by the reconstruction module 30. The predicted response that may be provided by the forward model 50 includes baseline assumptions that can influence the solution to the inverse problem.

The excitations are applied to the object 22 (shown in FIGS. 1 and 2) by the soft-field tomography instrument 54, which may include the transducers 24 and other excitation and measurement components, and thereafter measured voltages (measured data) are communicated to the reconstruction module 30. The soft-field reconstruction module 30 then performs reconstruction using various embodiments to generate an estimate of the property distribution 56, for example, the impedance distribution, to identify regions of interest 32 within the object 22 (both shown in FIG. 4). It should be noted that the various components may be physically separate components or elements or may be combined. For example, the soft-field reconstruction module 30 may form part of the soft-field tomography system 20 (as illustrated in FIG. 1).

Using various embodiments, soft-field reconstruction is provided that separates the contribution of the (i) geometry and (ii) material properties using responses from frequency varying or frequency and time varying excitations. Using differences in time or frequency responses as described in more detail herein, the contribution to the overall response from the material or impedance and the contribution from the geometry may be characterized or determined. For example, using the difference in the responses to the frequency varying excitations, any geometry error is suppressed as the geometry contribution to the overall response is largely frequency independent. Thus, geometry and electrode errors may be suppressed, such as rejecting the contribution of electrode geometry imperfections and mismatch to the forward model. Accordingly, the system error may be rejected to place emphasis on the response from the material properties within the object. Similarly, for a time varying excitation having a fixed frequency, the contribution to the overall response from non-time varying phenomenon and/or properties may be suppressed, as over time (e.g., 5 seconds) geometry and/or material properties may remain the same.

Figure 4:
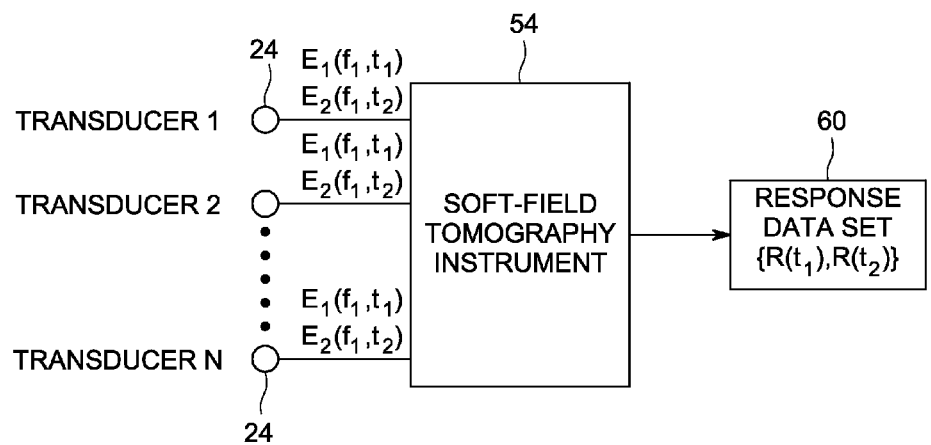
FIG. 4 is a simplified block diagram of a data acquisition process in accordance with an embodiment.

In particular, as illustrated in FIG. 4, in one embodiment, the soft-field tomography instrument 54 generates excitations at the transducers 24, which may be excitation currents that have a fixed frequency over time. For example, an alternating current excitation may be applied to the plurality of the transducers 24 to generate a field within the object 22 (shown in FIG. 1). The excitation applied at each of the transducers 24 has the same frequency, but may have different amplitudes and/or phases. Additionally, in this embodiment, multiple excitations having the same frequency $E(f_1)$ (e.g., 1 kHz) are applied over time to each of the transducers 24, for example, a first excitation at time $t_1$, $E_1(f_1,t_1)$ is applied followed by a second excitation at time $t_2$, $E_2(f_1,t_2)$, which may be a predetermined time period after the first excitation (e.g., 5 seconds). Thus, excitations $E_1(f_1,t_1)$ and $E_2(f_1,t_2)$ having the same frequency, but applied at different times are provided. In operation, a response is measured at each of the transducers 24 after application of each of the excitations. In this example, first and second responses are measured after the application of the first and second excitations to generate a response data set 60. The first and second excitations, thus, are varied in time, but fixed in frequency.

The response data set 60 may be generated by separating the responses, such as by determining a difference between the first and second responses. Accordingly, the difference in the response, R, at time $t_1$ and $t_2$ are determined to generate the response data set 60 (e.g., $R(t_1)-R(t_2)$). Thus, the contribution to the overall response from the material may be suppressed, if over time (e.g., 5 seconds) the material properties remain the same. It should be noted that in the various embodiments, the separation of the signals is not limited to a subtraction process. For example, any suitable signal separation technique may be used, such as signal division, scaling the responses, signal separation methods, among others.

Figure 5:
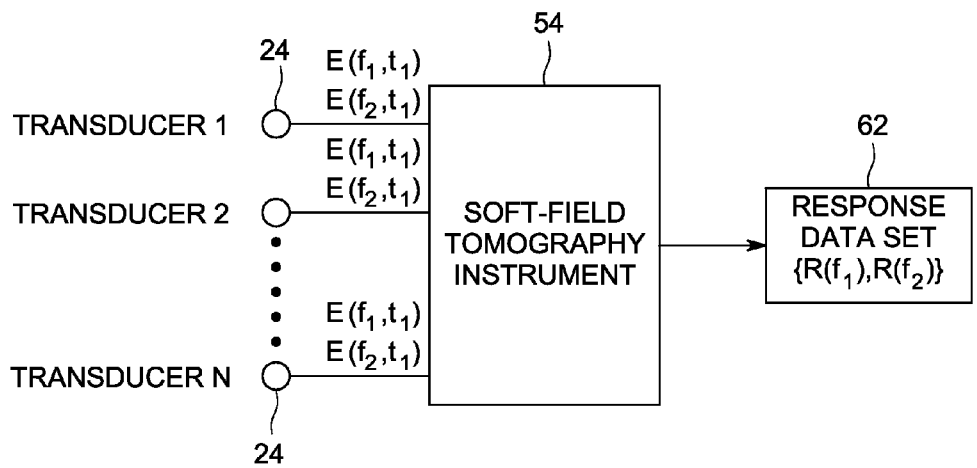
FIG. 5 is a simplified block diagram of a data acquisition process in accordance with another embodiment.

In accordance with another embodiment, as illustrated in FIG. 5, the soft-field tomography instrument 54 generates excitations at the transducers 24, which may be multiple excitation currents that have a varied frequency. For example, an alternating current excitation may be applied to the plurality of the transducers 24 to generate a field within the object 22 (shown in FIG. 1). The excitations applied at a plurality of the transducers 24 in this embodiment have different frequency components. For example, at a time $t_1$, multiple frequency component excitations are applied the transducers 24 at the same time, for example, simultaneously or concurrently, which in some embodiments, is an excitation signal formed from signal components at two different frequencies, $f_1$ and $f_2$ (e.g., 1 kHz and 100 Hz). Thus, one or more excitations, E, having multiple frequency components (e.g., E=E($f_1$,$t_1$)+E($f_2$,$t_1$)) are applied to the transducers 24. In operation, a response is measured at each of the transducers 24 after application of the excitation. In this example, the responses corresponding to each of the frequency components may be separated out to generate a response data set 62 using any suitable signal separation method. The excitation is, thus, applied at one point in time, but has multiple frequencies. The response data set 62 may be generated in one embodiment by determining a difference between the responses for each of the frequency components. Accordingly, the difference in the responses at time $t_1$ is determined to generate the response data set 62 (e.g., R($f_1$)−R($f_2$)). Thus, using the difference in the responses to the frequency varying excitations, any geometry error is suppressed as the geometry contribution to the overall response is largely frequency independent. Thus, geometry and electrode errors may be suppressed, such as rejecting the contribution of electrode geometry imperfections and mismatch.

Figure 6:
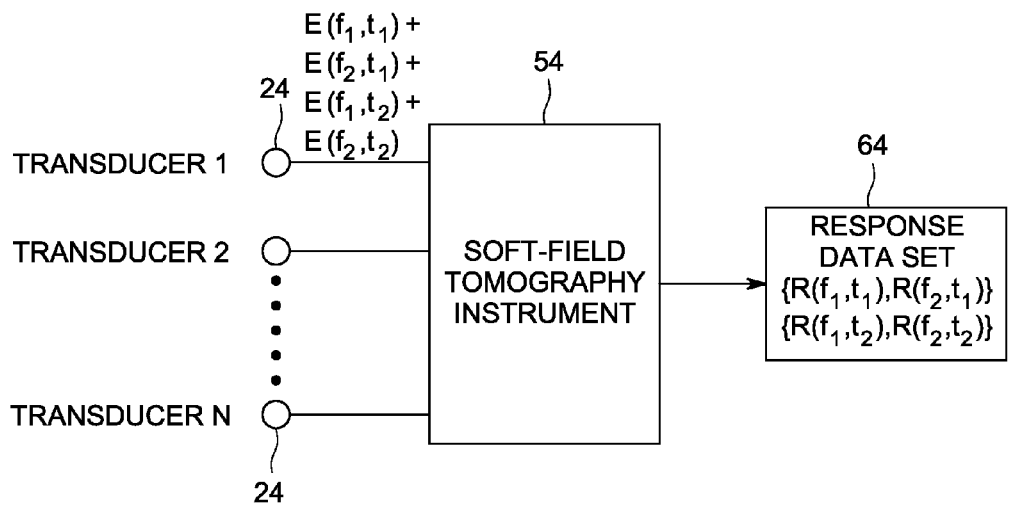
FIG. 6 is a simplified block diagram of a data acquisition process in accordance with another embodiment.

In accordance with another embodiment, as illustrated in FIG. 6, the soft-field tomography instrument 54 generates excitations at the transducers 24, which may be multiple excitation currents that have a varied frequency and are applied over time. For example, an alternating current excitation may be applied to the plurality of the transducers 24 to generate a field within the object 22 (shown in FIG. 1). The excitation applied at each of the transducers 24 has multiple frequencies (similar to the embodiment of FIG. 5) and is applied over time. It should be noted that the excitations applied to each of the transducers 24 may also have different amplitudes and/or phases. In this embodiment, multiple excitations having different frequency components $f_1$ (e.g., 1 kHz) and $f_2$ (e.g., 100 Hz), which are combined into a single excitation, are applied over time to each of the transducers 24, for example, a first excitation at time $t_1$ is applied followed by a second excitation at time $t_2$, which may be a predetermined time period after the first excitation (e.g., 5 seconds). Thus, in this non-limiting example, the excitation E=E($f_1$,$t_1$)+E($f_2$,$t_1$)+E($f_1$,$t_2$)+E($f_2$,$t_2$) is applied to the transducers 24. It should be noted that although the excitation is illustrated only with one transducer in FIG. 6, a similar excitation is applied to one or more of the other transducers 24. In operation, a response is measured at each of the transducers 24 after application of each of the excitations. In this example, first and second responses are measured after the application of the first and second excitations to generate a response data set 64. However, it should be noted that the application of the generated excitations and the measuring of the responses may be performed in any order (e.g., simultaneously, concurrently, in a sequence, etc.). The first and second excitations, thus, are varied in time and frequency. The response data set 64 may be generated by determining a difference between the first and second responses, which may include determining the difference in responses in time first, followed by the difference in separated frequency responses, or vice versa. Accordingly, the responses are separated, for example, the difference in the responses at time $t_1$ and time $t_2$ and also the differences in each of the frequency components $f_1$ and $f_2$ are determined to generate the response data set 64 (e.g., $R_1$=R($f_1$,$t_1$)−R($f_2$,$t_1$) and $R_2$=R($f_1$,$t_2$)−R($f_2$,$t_2$)). Thus, the contribution to the overall response from a material property and/or the transducer geometry may be suppressed.

Accordingly, in various embodiments two or more excitations are applied having one or more varied parameters. The responses to the two or more excitations are then used to determine or characterize the material property or impedance contribution versus the geometry contribution to the overall response.

Figure 7:
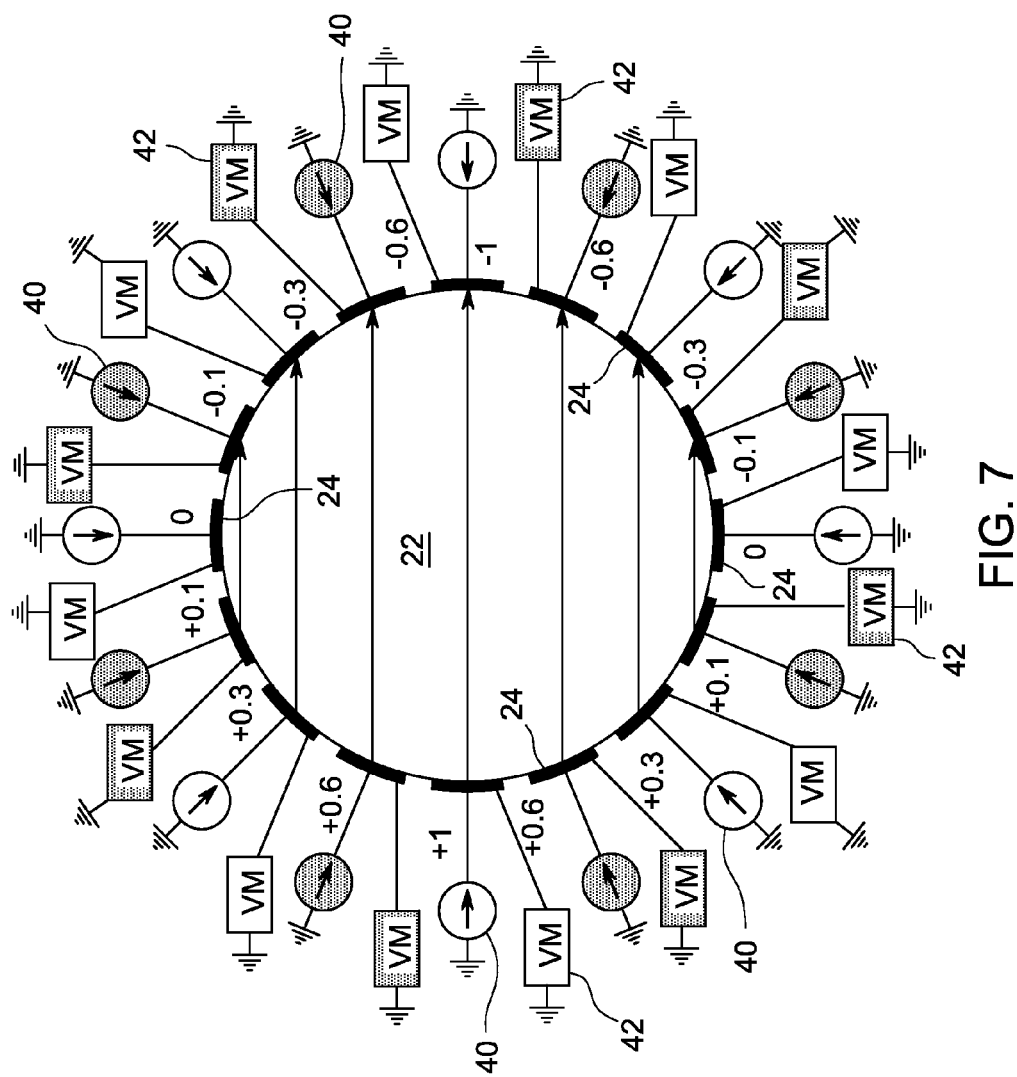
FIG. 7 is a simplified diagram illustrating one transducer configuration in accordance with various embodiments.

It should be noted that any suitable soft-tomography method for generating responses for the internal structure of the object 22 (shown in FIG. 1) may be used, such as with a processor defining a geometry of the object 22, and discretizing the geometry into a structure having a plurality of nodes and elements. Thus, as illustrated in one embodiment shown in FIG. 7, the excitation driver 26 applies an excitation on the geometry by providing an excitation, illustrated as an applied current 40, on each of the transducers 24 (e.g., electrodes), wherein the applied current 40 on each transducer 24 may be a single frequency or multi-frequency excitation signal. It should be noted that current and/or voltage sources may be provided, and may be more or less than the number illustrated. For example, each transducer 24, a set of the transducer 24 or all of the transducer 24 may share a current source or voltage source. The response detector 28 is illustrated as having a plurality of voltage measuring devices, such as voltmeters 42, for measuring a voltage at the electrodes 24. However, more or less voltmeters 42 or other measurement devices may be provided. It should be noted that the excitation and measured response (illustrated by the values around the periphery and by the arrows within the object 22) are simplified for illustration and the excitation and corresponding conductivity distribution may be more complex. Additionally, the illustrated values are again provided for simplicity and ease of understanding.

Figure 8:
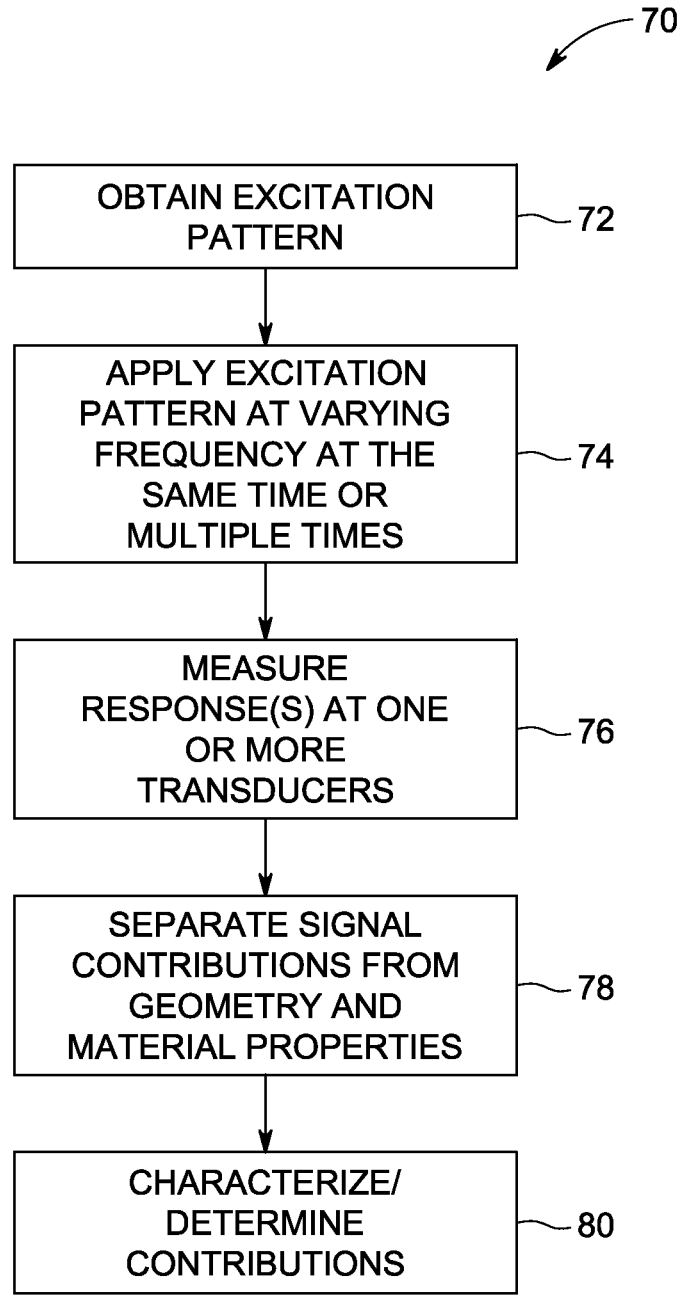
FIG. 8 is a flowchart of a method to generate excitations for a soft-field tomography system in accordance with various embodiments.

In various embodiments, a method 70 as illustrated in FIG. 8 is provided to generate excitations to determine the contribution to the overall response of the material or impedance of the object and/or the geometry. The method includes obtaining an excitation pattern at 72, which may include accessing a pre-computed excitation pattern (and also a corresponding pre-computed response). The excitation pattern is then applied to one or more transducers at 74, which may include applying multiple excitations over time that have the same frequency or multiple frequencies. The response at one or more transducers is then measured at 76.

Thereafter, the signal contributions from the geometry of the system and the material or impedance properties of the object are separated at 78 as described in more detail herein. This separation may include any suitable signal separation technique, for example, subtracting time difference received responses or different frequency component responses, or a combination thereof. The contributions then may be characterized or determined at 80, for example, calculating actual values or differences from baseline assumptions used, for example, in the forward model 50 (shown in FIG. 3).

It should be noted that the various embodiments including the method 70 may be performed on the output of data from different portions of the soft-field tomography system. For example, one or more of the artifact suppression methods described herein, including the signal separation, may be performed on one of signals that are (i) one or more outputs from the soft-field reconstruction module 30, (ii) one or more outputs from the soft-field tomography instrument 54 or (iii) one or more outputs from the forward model 50. Also, artifact suppression refers to the suppression of any artifact, for example, the suppression of contributions to the overall response that are not of interest.

Accordingly, using time and/or frequency differences in the measured responses to separate transducer, geometry, boundary and/or surface contributions to the measured response from material property contributions to the measured response may be performed on the predicted responses or using the output from the soft-field reconstruction module 30, instead of or in addition to the measured responses.

For example, predicted responses may be generated using the forward model 50 to one or more frequencies at one or more times. This data can be used with any type of measurement data (e.g., multiple frequencies f at a single time t, multiple times t at a single frequency f, multiple time t at multiple frequencies f, etc.). As another example, two complete reconstructions may be performed first using the predicted responses to frequency 1 and measured responses from frequency 1 and the second using predicted responses to frequency 2 and measured responses from frequency 2. The separation of the signals, for example, the difference operation can then be performed on the output from the two reconstructions.

Although separating (i) an object material property or impedance contribution and (ii) a geometry contribution from an overall response is described herein, variations and modifications are contemplated. For example, (i) multiple material property (e.g., impedance) contributions or (ii) multiple geometry contributions also may be separated from the overall response.

Thus, a response of the geometry to the applied excitation is determined, wherein the geometry is defined as the shape of the boundary of the object, the location of the transducers and the assumed conductivity distribution inside the object, as described in more detail herein, with suppression of artifacts, among others. For example, various embodiments provide a method to identify and suppress artifacts related to differences between the modeled and actual geometry and transducer arrangement.

In various embodiments, predetermined excitations are applied to the transducers and responses measured, wherein the excitations may comprise single (pure) or multiple frequencies or tones and may be applied simultaneously or sequentially such that various frequency components or tones are applied at the same or different points in time. The measured responses may be combined using an algorithm in raw form (e.g., subtraction of temporally synchronous signals acquired at different frequencies) or reconstructed and then combined.

The various embodiments and/or components, for example, the modules, elements, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), field-programmable gate arrays (FPGAs), graphical processing units (GPUs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software", "firmware" and "algorithm" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for acquiring soft-field tomography data, the method comprising:
   obtaining an excitation pattern having a plurality of frequency components;
   applying the excitation pattern to an object;
   measuring an overall response at a transducer coupled to the object, wherein the overall response includes an artifact and a plurality of responses corresponding to the plurality of frequency components; and
   separating the overall response to suppress the artifact.

2. The method of claim 1, wherein the overall response is measured for the excitation pattern, which is applied at one point in time.

3. The method of claim 1, wherein applying the excitation pattern comprises applying an excitation signal wherein the plurality of frequency components are applied simultaneously.

4. The method of claim 1, further comprising combining the plurality of frequency components into a single excitation signal.

5. The method of claim 4, wherein the single excitation signal is an alternating current.

6. The method of claim 1, wherein the overall response is measured of the object to the excitation pattern, which is applied at a plurality of points in time.

7. The method of claim 6, wherein separating comprises determining a difference in the overall response based on time and frequency.

8. The method of claim 7, wherein determining the difference comprises subtracting one response from another response among the plurality of responses.

9. The method of claim 1, wherein the excitation pattern comprises two or more excitations.

10. The method of claim 1, further comprising using the measured overall response to determine a property distribution of the object.

11. The method of claim 10, wherein the property distribution is a distribution as determined in one of Electrical Impedance Spectroscopy (EIS), Electrical Impedance Tomography (EIT), Diffuse Optical Tomography (DOT), Near InfraRed Spectroscopy (NIRS), thermography, elastography or microwave tomography.

12. The method of claim 10, wherein the property distribution comprises a distribution of one or more of electric conductivity, electric permittivity, magnetic permeability, optical absorbance, optical scattering, optical reflectivity, elasticity, or thermal conductivity.

13. The method of claim 1, further comprising separating from the overall response (i) an object material property contribution and (ii) a geometry contribution.

14. The method of claim 1, wherein the separating is performed on one of signals that are (i) one or more outputs from a reconstruction module, (ii) one or more outputs from a soft-field tomography instrument or (iii) one or more outputs from a forward model.

15. A soft-field tomography system comprising:
   a plurality of transducers configured for positioning proximate a surface of an object;
   one or more excitation drivers coupled to the plurality of transducers and configured to generate excitation signals for the plurality of transducers, wherein the excitation signals include a plurality of frequency components;
   one or more response detectors coupled to the plurality of transducers and configured to measure a response of the object at the plurality of transducers to the excitation applied by the plurality of transducers based on the excitation signals; and
   a soft-field reconstruction module configured to reconstruct a property distribution based on the excitation signals and the measured response based in part on a difference between the responses among the plurality of frequency components.

16. The soft-field tomography system of claim 15, wherein the one or more excitation drivers are configured to generate excitations signals applying the plurality of frequency components one of concurrently, simultaneously or sequentially to the plurality of transducers.

17. The soft-field tomography system of claim 15, wherein the soft-field reconstruction module is configured to reconstruct a property distribution based on a difference among responses to excitations applied at different times.

18. The soft-field tomography system of claim 15, wherein the property distribution is a distribution as determined in one or more of Electrical Impedance Spectroscopy (EIS), Electrical Impedance Tomography (EIT), Diffuse Optical Tomography (DOT), Near InfraRed Spectroscopy (NIRS), thermography, elastography or microwave tomography.

19. The soft-field tomography system of claim 15, wherein the property distribution comprises a distribution of one or more of electric conductivity, electric permittivity, magnetic permeability, optical absorbance, optical scattering, optical reflectivity, elasticity, or thermal conductivity.

20. A computer readable storage medium for acquiring soft-field tomography data and reconstructing a property distribution of an object using a processor, the computer readable storage medium including instructions to command the processor to:
   obtain an excitation pattern;
   apply the excitation pattern to an object, wherein the excitation pattern includes a plurality of frequency components;
   measure a response at one or more of a plurality of transducers coupled to the object;
   determine a difference between the responses for each of the plurality of frequency components; and
   use the measured response and the difference to reconstruct a property distribution of the object.

21. The computer readable storage medium of claim 20, wherein the instructions command the processor to use measured responses for excitation patterns applied at different times.

* * * * *